United States Patent [19]

Terada et al.

[11] 4,011,138

[45] Mar. 8, 1977

[54] PROCESS FOR THE PREPARATION OF CHOLESTEROL ESTERASE

[75] Inventors: Osamu Terada; Takayuki Uwajima, both of Machida, Japan

[73] Assignee: Kyowa Hakko Kogyo Co., Ltd., Tokyo, Japan

[22] Filed: June 17, 1975

[21] Appl. No.: 587,699

[30] Foreign Application Priority Data

June 17, 1974 Japan .............................. 49-68160

[52] U.S. Cl. ................................ 195/65; 195/66 R
[51] Int. Cl.$^2$ ........................................ C12D 13/10
[58] Field of Search ............. 195/65, 66 R, 103.5 R

[56] References Cited

UNITED STATES PATENTS 3,869,349  3/1975  Goodhue et al. ............ 195/103.5 R

FOREIGN PATENTS OR APPLICATIONS 1,185  1/1973  Japan

OTHER PUBLICATIONS

Chemical Abstracts, vol. 78, 96093s (1973).

*Primary Examiner*—Lionel M. Shapiro
*Attorney, Agent, or Firm*—Fitzpatrick, Cella, Harper & Scinto

[57] ABSTRACT

Cholesterol esterase is prepared by fermentation of a microorganism capable of producing cholesterol esterase and belonging to the genus Pseudomonas. Cholesterol esterase is useful for the determination of total serum cholesterol.

13 Claims, 4 Drawing Figures

PROCESS FOR THE PREPARATION OF CHOLESTEROL ESTERASE

BACKGROUND OF THE INVENTION

This invention relates to the process for the preparation of cholesterol esterase and more specifically to the process for the preparation of cholesterol esterase by fermentation of a cholesterol esterase-producing microorganism of the genus Pseudomonas.

Cholesterol esterase (E C 3.1.1.13) is an enzyme which catalyzes the hydrolysis of cholesterol esters into cholesterol and fatty acids, and is known to be distributed widely in animals and plants.

Recently, it has been proposed to use cholesterol esterase in the determination of total serum cholesterol [Clinical Chemistry, Vol 20, No. 4 pages 470–475 (1974)]. The determination of total cholesterol in serum is important for diagnostic purposes in connection with arteriosclerosis, cerebral hemorrhage and hepatic disorders.

Cholesterol exists in the free form and ester form in serum. In the proposed determination method, a sample of serum is treated with cholesterol esterase and cholesterol oxidase. In this treatment, cholesterol esters in the sample are hydrolyzed into free cholesterol and fatty acids, and free form cholesterol in the serum and the liberated cholesterol are oxidized into cholestenone generating hydrogen peroxide. The total cholesterol can be determined by measuring oxygen uptake, cholestenone or hydrogen peroxide by a conventional method. The above method is simple and convenient and therefore is considered to be applicable to the practical assay.

As is already mentioned, cholesterol esterase is known to be widely distributed in natural sources. However, a development of a process of the commercial production of the enzyme is now in demand. The present inventors have carried out studies on the fermentative production of cholesterol esterase by microorganisms. The present inventors initially carried out the screening of cholesterol esterase producers from various bacteria based on the test on the utilization of cholesterol esters and subsequent test on the productivity of cholesterol esterase. As the result, the present inventors have found that good cholesterol esterase producers are found among microorganisms of the genus Pseudomonas, particularly, those of the species *Pseudomonas fluorescens*.

SUMMARY OF THE INVENTION

According to the present invention, it has been found that when a microorganism belonging to the genus Pseudomonas is cultured in a nutrient medium, a remarkable amount of cholesterol esterase is produced both extracellularly and intracellularly.

DESCRIPTION OF THE INVENTION

Figure 1:
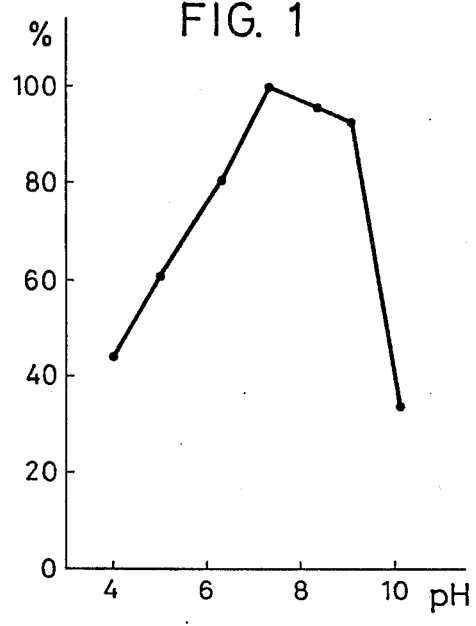
FIG. 1 illustrates the activity of cholesterol esterase prepared by the process of the present invention at different pH values between 4 and 10.

In accordance with the present invention, any microorganism capable of producing cholesterol esterase and belonging to the genus Pseudomonas can be used. Particularly preferred microorganisms are found among those of the species *Pseudomonas fluorescens*. The examples of favorable producers are *Pseudomonas fluorescens* KY 3955 (FERM-P No. 2611) ATCC 31156, *Pseudomonas fluorescens* KY 3956 IAM 1051, *Pseudomonas fluorescens* KY 3975 IFO 3903 ATCC 948, *Pseudomonas fluorescens* KY 4032 and *Pseudomonas fluorescens* KY 4033 IFO 3081. FERM-P means a deposit of a microorganism with the Fermentation Research Institute, Chiba-ken, Japan, ATCC is an abridgment of the American Type Culture Collection, Rockville, MD, U.S.A., IAM is an abridgment of the Institute of Applied Microbiology, Tokyo University, Tokyo, Japan and IFO is an abridgment of the Institute for Fermentation, Osaka, Japan.

The genus Pseudomonas and the species *Pseudomonas fluorescens* are described in Bergey's Manual of Determinative Bacteriology, 8th Ed., published by Williams and Wilkins Co.

In carrying out the culturing of the process of the present invention, either a synthetic medium or natural medium may be used so long as it properly contains a carbon source, a nitrogen source, inorganic materials and other nutrients.

As the carbon source, carbohydrates such as glucose, fructose, sucrose, maltose, mannose, starch, starch hydrolyzate, molasses, etc., sugar alcohols such as glycerol, sorbitol, mannitol, etc., organic acids such as acetic acid, lactic acid, pyruvic acid, fumaric acid, citric acid, etc., alcohols such as methanol, ethanol, etc., glycols such as ethylene glycol, propylene glycol, etc., hydrocarbons such a n-paraffins, etc. and various amino acids may be used depending upon the utilization by the microorganisms to be employed. Further, as is understood from the screening procedure of the microorganisms, cholesterol esters can also be used as a carbon source.

As the nitrogen source, ammonia, inorganic and organic ammonium salts such as ammonium chloride, ammonium carbonate, ammonium phosphate, ammonium nitrate, ammonium acetate, etc., nitrogen-containing compounds such as urea, amino acids, etc., nitrogenous organic materials such as peptone, NZ-amine (trade name for enzymatic hydrolyzate of casein available from Sheffield Chemical Company, U.S.A.), meat extract, corn steep liquor, casein hydrolyzate, chrysalis hydrolyzate, fish meal, digested fish meal, soybean meal, digested soybean meal, etc., may be used depending upon the utilization of the microorganisms to be employed. It is to be understood that some of nitrogen sources may be used also as a carbon source.

As the inorganic materials, potassium dihydrogen phosphate, dipotassium hydrogen phosphate, magnesium sulfate, sodium chloride, ferrous sulfate, manganese sulfate, potassium chloride, calcium carbonate, etc., may be used.

If a microorganism to be employed in the present invention requires specific nutrients for growth, appropriate amounts of such nutrients must, of course, be supplemented to the medium. Sometimes, the nitrogeneous organic materials to be employed as the nitrogen source may also serve as the source of the required nutrients. When such nitrogenous organic materials are employed, it is not necessary that the required nutrients be separately supplemented to the medium.

Various medium compositions may be considered combining the above-mentioned sources and materials. However, it has been found that the strains of *Pseudomonas fluorescens* which are useful in the present invention produce only a trace amount of cholesterol esterase in an ordinary nutrient medium but they produce a remarkable amount of cholesterol esterase when cultured in a medium containing cholesterol esters. Therefore, a cholesterol ester is to be present in the medium, and the ester may serve also as a sole or partial source of carbon. As the suitable cholesterol esters, cholesterol stearate, cholesterol palmitate, cholesterol laurate, cholesterol oleate and cholesterol linoleate are mentioned.

Generally, it is preferable that at least 0.3% by weight of cholesterol esters based on the volume of the medium are present in the medium.

It has also been found that the use of soybean flour or soybean meal as a constituent of the medium with or without cholesterol esters gives good result for the production of cholesterol esterase according to the process of the present invention. Particularly good results are obtained when the medium contains 0.3–7%, preferably about 2% by weight of soybean meal based on the volume of the medium.

It has further been found that much better results can be obtained when soybean meal or soybean flour is used in combination with fatty acids or fatty acid esters. Such fatty acids and fatty acid esters are exemplified by stearic acid, linoleic acid, oleic acid, triolein, trilinolein, soybean oil, rice bran oil, rapeseed oil, olive oil, etc.

It is preferable that the fatty acids and the fatty acid esters are used in an amount of 0.3 – 1.5% by weight based on the volume of the medium.

Culturing is carried out under aerobic conditions, for example, by shaking culture or by aeration agitation submerged culture at a temperature of 20° to 40° C. During the culturing, the pH is maintained at 3–9, preferably, 6–8. Usually, after 1 to 5 days of culturing, cholesterol esterase is produced and accumulated extracellularly and also intracellularly.

After the completion of culturing, cholesterol esterase is isolated and purified from the microbial cells and from the filtrate of the culture liquor by any of the conventional methods. For example, microbial cells are separated from the culture liquor by filtration. The filtrate is concentrated under reduced pressure at a temperature below 40° C. To the concentrate is added ammonium sulfate to about 60% saturation with stirring and the mixture is allowed to stand. The resulted precipitates are separated by filtration and dissolved in 5 to 10 times the volume of the precipitates of 0.01M phosphate buffer (pH 7.0). The solution is passed through a column of Sephadex G-25 (trade name for molecular shieve, derivatives of polysaccharide dextran, available from Pharmacia Fine Chemicals Inc., U.S.A.) for desalting and fractionation. The active fractions are combined and charged onto a column of DEAE cellulose. After washing the column with 0.1M phosphate buffer (pH 7.0), elution is carried out with 0.1M phosphate buffer (pH 7.0) containing 0.1M NaCl. Active fractions are combined and concentrated under reduced pressure. The concentrate is dialyzed against 0.01M phosphate buffer for desalting and is freeze-dried to obtain a purified preparation of cholesterol esterase.

In isolating and purifying cholesterol esterase from microbial cells, the separated cells are disrupted with a ball mill and suspended in an appropriate amount of 0.01M phosphate buffer (pH 7.0). The suspension is subjected to centrifugation and the supernatant is treated in the same manner as described above in connection with the isolation and purification of cholesterol esterase from the culture filtrate.

Cholesterol esterase prepared by the process of the present invention is characterized by the following enzymatic properties.

1. Substrate specificity

Cholesterol esterase prepared by the process of the present invention catalyzes the hydrolysis of various cholesterol esters and particularly, shows the strongest action on cholesterol linoleate.

The determination of the enzyme activity on cholesterol linoleate is carried out by the following method.

A mixture having the following composition is prepared and shaken at 37° C for 30 minutes.

| | |
|---|---|
| 1% Solution of cholesterol linoleate in ethanol | 0.1 ml |
| 0.1M Phosphate buffer (pH 7.5) | 0.1 ml |
| 0.01M Phosphate buffer (pH 7.5) solution of cholesterol oxidase produced by *Brevibacterium sterolicum* ATCC 21387, the solution containing 20 international units/ml of the enzymatic activity | 0.05 ml |
| Enzyme solution to be determined | 0.1 ml |

During the above-described operation, the substrate cholesterol linoleate is hydrolyzed by the action of cholesterol esterase into cholesterol and linoleic acid, and subsequently the formed cholesterol is oxidized to cholestenone by the action of cholesterol oxidase. After 30 minutes of shaking, the mixture is immediately subjected to the determination of residual unreacted cholesterol linoleate by Zurkowsky's method [Clinical Chemistry 10, 451 (1964)]. Then, the amount of the reacted cholesterol linoleate is calculated. The enzyme activity is expressed by "unit." A "unit" of enzyme activity is defined as that amount of enzyme which will decompose 1 μmole of cholesterol linoleate in 1 minute under the above-described conditions. The enzyme activities on other cholesterol esters are variable depending upon the kind of substrates and are determined in the similar manner.

Table 1 shows relative activities of cholesterol esterase of the present invention on various cholesterol esters, the activity on cholesterol linoleate being defined as 100.

Table 1

| Substrate | Relative activity |
|---|---|
| Cholesterol linoleate | 100 |
| Cholesterol oleate | 93 |
| Cholesterol acetate | 80 |
| Cholesterol stearate | 58 |
| Cholesterol palmitate | 26 |

The enzyme activity of cholesterol esterase at different pH values between 4 and 10 is determined according to the method described above. The results are shown in FIG. 1 of the accompanying drawings. In FIG. 1, the enzyme activity is indicated in percent relative to the maximum activity. As is seen from FIG. 1, the optimum pH of the enzyme activity is around 7.3.

3. Stable pH range

Figure 2:
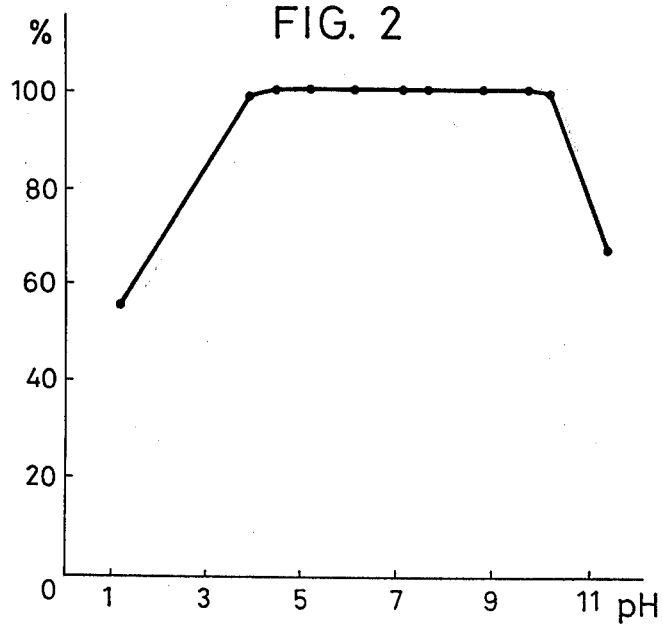
FIG. 2 illustrates the stability of cholesterol esterase prepared by the process of the present invention at different pH values between 1 and 11 at 37° C after an exposure time of 30 min.

The stable pH range of the enzyme activity is examined. The enzyme is dissolved in phosphate buffers having different pH values between 1 and 11 at a concentration of 0.1 mg/ml. The thus prepared enzyme solutions are kept at 37° C for 30 minutes. The residual enzyme activity (%) of the solution is determined. The results are shown in FIG. 2 of the accompanying drawings. As is seen from FIG. 2, the enzyme is stable at a pH between 4 and 10 under the test conditions.

4. Optimum temperature

Figure 3:
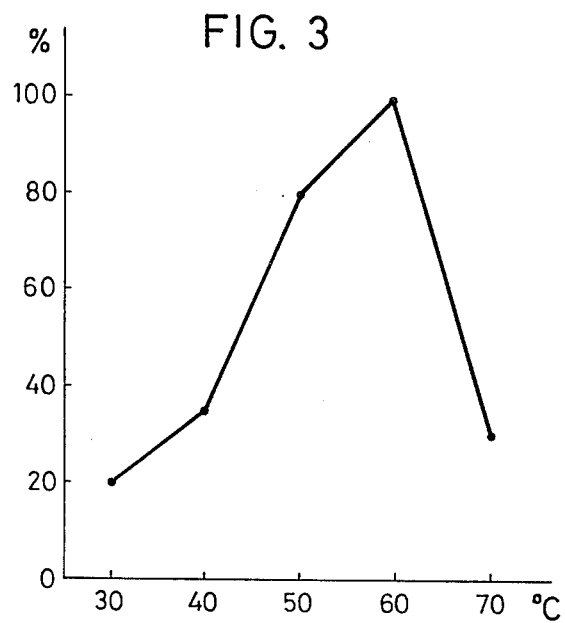
FIG. 3 illustrates the activity of cholesterol esterase prepared by the process of the present invention at different temperatures between 30° and 70° C.

The activity of the enzyme at different temperatures between 30° and 70° C is determined. The results are shown in FIG. 3 of the accompanying drawings in which the enzyme activity is indicated in percent relative to the maximum activity. As is seen from FIG. 3, the optimum temperature for the enzyme activity is around 60° C.

5. Stable temperature range

Figure 4:
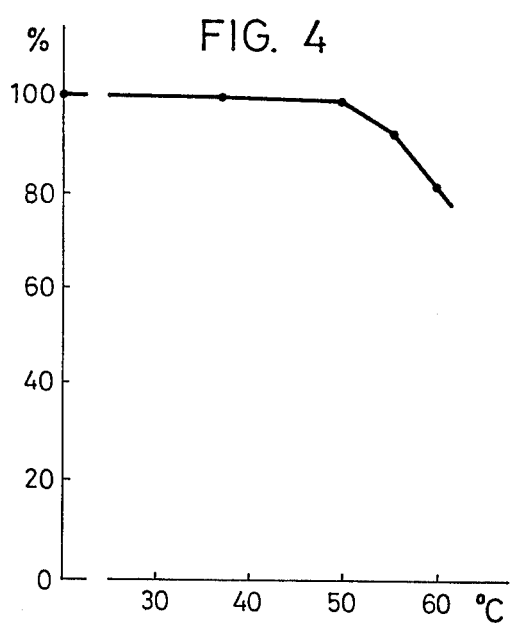
FIG. 4 illustrates the stability of cholesterol esterase prepared by the process of the present invention at different temperatures between 0° and 60° C at pH 7.0 after an exposure time of 30 min.

The stable temperature range of the enzyme activity is examined. The enzyme is dissolved in a phosphate buffer having a pH of 7.0 at a concentration of 0.1 mg/ml. The thus prepared enzyme solutions are kept at different temperatures between 0° and 60° C for 30 minutes. Thereafter, the residual enzyme activity (%) is determined. The results are shown in FIG. 4 of the accompanying drawings. As is seen from FIG. 4, the enzyme is very stable at a temperature below 50° C at pH 7.0 after an exposure time of 30 minutes.

6. Inhibitors

Inhibitory effects of various substances on the enzyme activity are examined. The enzyme is dissolved in 0.01M phosphate buffer at a concentration of 0.1 mg/ml. To 0.1 ml of the solution are added 0.1 ml of 0.1M phosphate buffer and 0.1 ml of 4 mM solution of various substances shown in Table 2 and the mixture is kept at 37° C for 15 minutes. Thereafter, 0.1 ml of 1% solution of cholesterol linoleate in ethanol is added to the mixture and the resulting mixture is allowed to stand at 37° C for 10 minutes. The mixture is then heated at 100° C for 3 minutes to inactivate the enzyme and subjected to silica gel thin layer chromatography. Development is carried out with a mixture of n-hexane, methanol and acetone (50 : 5 : 1). The spot of cholesterol is detected at Rf 0.8 with U.V. light. The spot portion of the silica gel is taken out and extracted with ethanol.

The amount of cholesterol in the extract is determined according to Zurkowsky's method. Then, the amount of residual cholesterol linoleate is calculated. The inhibitory effect is expressed by inhibition ratio which is the ratio of the residual cholesterol linoleate to the initial cholesterol linoleate. The results are shown in Table 2.

Table 2

| Inhibitor | Inhibition ratio (%) |
| --- | --- |
| $AgNO_3$ | 20 |
| $HgCl_2$ | 100 |
| $CuSO_4$ | 100 |
| p-Chloromercuri benzoic acid (p-CMB) | 0 |
| $CaCl_2$ | 0 |

Table 2-continued

| Inhibitor | Inhibition ratio (%) |
| --- | --- |
| $BaCl_2$ | 0 |
| $ZnCl_2$ | 0 |
| $FeSO_4$ | 0 |
| $MnCl_2$ | 0 |
| Diisopropyl phosphofluoridic acid | 0 |
| Ethylenediaminetetraacetic acid | 0 |
| o-Phenanthroline | 0 |
| 2,2'-Dipyridyl | 0 |

As is apparent from the above table, the activity of the present enzyme is inhibited by heavy metal ions such as $Cu^{++}$, $Hg^{++}$ and $Ag^+$.

7 Ultra-centrifugal analysis

The enzyme of the present invention is subjected to ultra-centrifugal analysis according to the method of Schachman [Ultra-centrifugation in Biochemistry, Academic Press Inc., London and New York (1959)]. The sedimentation pattern shows that the enzyme is almost homogeneous.

8. Molecular weight

The molecular weight of the enzyme of the present invention is determined according to the gel-filtration method [Biochemical Journal 96 595 (1965)] using Sephadex G 100. As the result, the enzyme is determined to have a molecular weight of about 125,000.

Now the present invention is further illustrated by the following examples, but the scope of the present invention is not limited thereto.

EXAMPLE 1

In this example, one loopful of Pseudomonas fluorescens KY 3955 (FERM-P No. 2611) ATCC 31156 is inoculated into 300 ml of a medium having the following composition in a 2 l-Erlenmeyer flask provided with baffles.

| | |
| --- | --- |
| Cholesterol linoleate | 5 g/l |
| Corn steep liquor | 2 g/l |
| $NaNO_3$ | 2 g/l |
| $K_2HPO_4$ | 1 g/l |
| KCl | 0.5 g/l |
| $MgSO_4 \cdot 7H_2O$ | 0.5 g/l |
| (pH 7.5 before sterilization | |

Culturing is carried out with shaking at 30° C for 30 hours. After the completion of culturing, the culture liquor is subjected to filtration. The filtrate (270 ml) exhibits a cholesterol esterase activity of 4.5 units. The wet cells (5 g) are disrupted with a ball mill. The disrupted cells are suspended in 0.01M phosphate buffer (pH 7.0). The suspension is subjected to centrifugation. The resulting cell-free extract exhibits an enzyme activity of 0.35 unit.

EXAMPLE 2

In this example, Pseudomonas fluorescens KY 3955 (FERM-P No. 2611) ATCC 31156 is initially grown in a bouillon medium (pH 7.2) comprising 10 g/l of meat extract, 10 g/l of peptone and 5 g/l of NaCl at 30° C for 48 hours. 750 ml of the thus prepared seed culture is inoculated into 15 l of a medium having the following composition in a 30 l-jar fermenter.

| | |
| --- | --- |
| Soybean meal | 20 g/l |
| Glucose | 3 g/l |
| $NaNO_3$ | 2 g/l |

| | |
|---|---|
| K$_2$HPO$_4$ | 1 g/l |
| KCl | 0.5 g/l |
| MgSO$_4$ . 7H$_2$O | 0.5 g/l |
| (pH 7.5 before sterilization) | |

Culturing is carried out with aeration of 15 l/min. and stirring at 400 r.p.m. at 30° C for 24 hours. After the completion of culturing, the culture liquor is subjected to filtration. The filtrate (15 l) exhibits a cholesterol esterase activity of 253 units.

EXAMPLE 3

In this example, 14.6 l of a filtrate (exhibiting a cholesterol esterase activity of 225 units) obtained in the same manner as described in Example 2 is concentrated to 5 l under reduced pressure at a temperature below 40° C. To the concentrate is added 1.9 kg of ammonium sulfate (corresponding to 60% saturation) with stirring and the mixture is allowed to stand overnight in a refrigerator to obtain precipitates.

To the resulting mixture containing precipitates is then added 500 g of a filter aid (Radiolite available from Showa Kagaku Kogyo Co., Ltd., Japan) and the mixture is filtered. The filter cake is added to 300 ml of 0.01M phosphate buffer (pH 7.0) to dissolve the soluble matters and the mixture is subjected to filtration.

The filtrate is passed through a column (diameter: 10 cm, height: 100 cm) packed with Sephadex G-25 suspended in 0.01M phosphate buffer (pH 7.0). The effluent is obtained in fractions and the active fractions are combined and passed through a column (diameter: 7cm, height: 60 cm) of DEAE-cellulose suspended in 0.01M phosphate buffer (pH 7.0) to adsorb the active principle thereof. The column is washed with 0.01M phosphate buffer (pH 7.0). Thereafter, elution is carried out with 0.1M phosphate buffer (pH 7.0) containing 0.1M NaCl.

The active fractions are combined and concentrated to about 100 ml under reduced pressure at a temperature below 40° C. The concentrate is dialyzed against 0.01M phosphate buffer (pH 7.0) and freeze-dried to obtain 1.2 g of a product of cholesterol esterase. The product exhibits a specific activity of 0.105 unit/mg of protein.

At each step of purification, protein, and total activity are assayed and the specific activity and the yield of cholesterol esterase are examined. The results are shown in Table 3.

Table 3

| | Amount of protein (mg) | Total activity (unit) | Specific activity (unit/mg of protein) | Yield (%) |
|---|---|---|---|---|
| Filtrate | 32,200 | 225 | 0.007 | 100 |
| Concentrate of filtrate | 30,600 | 214 | 0.007 | 95 |
| Ammonium sulfate-precipitate | 15,000 | 180 | 0.012 | 80 |
| Active fractions from Sephadex G-25-column | 10,000 | 170 | 0.017 | 75 |
| Active fractions from DEAE-cellulose-column | 1,120 | 118 | 0.105 | 52 |
| Freeze-dried-product | 1,050 | 110 | 0.105 | 49 |

EXAMPLE 4

225 of the wet cells obtained in Example 2 are disrupted with a ball mill. The disrupted cells are suspended in about 1 l of 0.01M phosphate buffer (pH 7.0). The suspension is subjected to centrifugation and the supernatant is treated in the same manner as described in Example 3. As the result, 98 mg of a product of purified cholesterol esterase having a specific activity of 0.101 unit/mg of protein is obtained. At each step of purification, protein and total activity are assayed and the specific activity and the yield of cholesterol esterase are examined. The results are shown in Table 4.

Table 4

| | Amount of protein (mg) | Total activity (unit) | Specific activity (unit/mg of protein) | Yield (%) |
|---|---|---|---|---|
| Cell extract | 6,000 | 18.0 | 0.003 | 100 |
| Ammonium sulfate-precipitate | 5,250 | 15.5 | 0.003 | 86 |
| Active fractions from Sephadex G-25-column | 1,400 | 14.0 | 0.010 | 78 |
| Active fractions from DEAE-cellulose-column | 106 | 10.8 | 0.102 | 60 |
| Freeze-dried-product | 98 | 9.9 | 0.101 | 55 |

EXAMPLE 5

In this example, the procedure described in Example 2 is repeated except that various fatty acids and fatty acid esters shown in Table 5 are added to the fermentation medium at a concentration of 5 g/l. The cholesterol esterase activities of the resulted culture filtrates are shown in Table 5.

Table 5

| Additives | ACtivity (unit/l) |
|---|---|
| linoleic acid | 310 |
| oleic acid | 170 |
| stearic acid | 230 |
| soybean oil | 290 |
| rice bran oil | 300 |
| rapeseed oil | 130 |
| olive oil | 180 |
| triolein | 200 |
| trilinolein | 250 |
| None | 20 |

EXAMPLE 6

In this example, the procedure in Example 2 is repeated except that four strains shown in Table 6 are used in place of *Pseudomonas fluorescens* ATCC 31156. The cholesterol esterase activities of the resulted culture filtrates are shown in Table 6.

Table 6

| Strains | Activity (unit/l) |
|---|---|
| *Pseudomonas fluorescens* KY 3956 IAM 1051 | 3.4 |
| *Pseudomonas fluorescens* KY 3975 IFO 3903 ATCC 948 | 1.7 |
| *Pseudomonas fluorescens* KY 4032 | 1.7 |
| *Pseudomonas fluorescens* | |

Table 6-continued

| Strains | Activity (unit/l) |
|---|---|
| KY 4033 IFO 3081 | 1.7 |

DETERMINATION OF TOTAL CHOLESTEROL IN SERUM

Determination of total cholesterol in serum is carried out based on the description in Clinical Chemistry, Vol. 20, No. 4 (1974) using the cholesterol esterase obtained by the process of the present invention.

0.02 ml of each of commercially available control serum samples shown in Table 7 is added to 3.0 ml of 0.1M phosphate buffer (pH 6.7) containing 3.0 mM sodium cholate, 0.82 mM 4-aminoantipyrine, 14 mM phenol, 67,000 units/l of peroxidase (product available from Worthington Biochemical Corp., U.S.A.), 117 units/l of cholesterol oxidase (produced by culturing *Brevibacterium sterolicum* ATCC 21387), 0.17 mM of Carbowax-6000 (a trade name for surfactant available from Schwarz/Mann Research Laboratories, U.S.A.), and 33 units/l of cholesterol esterase. The mixture is allowed to stand for 15 minutes at 37° C and further for about 10 minutes at room temperature. Then, the absorbancy at 500 nm of the mixture is measured against a reagent blank. The concentration of total cholesterol in the samples is determined from a standard curve constructed by using cholesterol standards. For the reference, free cholesterol in the control serum samples is determined in a similiar manner wherein no cholesterol esterase is employed. The results are also shown in Table 7.

Table 7

| Control Serum | Concentration of cholesterol (mg/dl) | | | |
|---|---|---|---|---|
| | Total | | Free | |
| | Assigned | Determined | Assigned | Determined |
| 1. Q-PAK-Chemistry Control Serum I * | 175 | 180 | 37 | 31 |
| 2. Q-PAK™-Chemistry Control Serum II * | 150 | 158 | 36 | 32 |
| 3. Seraclear ** | 191 | 202 | 44 | 47 |

* available from HYLAND DIVISION TRAVENOL LABORATORIES, Inc., U.S.A.
** available from WARNER-LAMBERT Co., U.S.A.

What is claimed is:

1. A process for preparing cholesterol esterase which comprises culturing a microorganism belonging to the species *Pseudomonas fluorescens* and capable of producing cholesterol esterase in a nutrient medium, producing and accumulating cholesterol esterase extracellularly and intracellularly, and recovering said cholesterol esterase.

2. The process of claim 1 wherein said microorganism is selected from *Pseudomonas fluorescens* KY 3955 (FERM-P No. 2611) ATCC 31156, *Pseudomonas fluorescens* KY 3956 IAM 1051, *Pseudomonas fluorescens* KY 3975 IFO 3903 ATCC 948, *Pseudomonas fluorescens* KY 4032 and *Pseudomonas fluorescens* KY 4033 IFO 3081.

3. The process of claim 1 wherein said nutrient medium contains at least one fatty acid ester of cholesterol.

4. The process of claim 3 wherein said fatty acid ester of cholesterol is selected from cholesterol stearate, cholesterol palmitate, cholesterol laurate, cholesterol oleate and cholesterol linoleate.

5. The process of claim 3 wherein said nutrient medium contains at least 0.3% by weight of the fatty acid ester of cholesterol based on the volume of the nutrient medium.

6. A process for preparing cholesterol esterase which comprises culturing a microorganism belonging to the genus Pseudomonas and capable of producing cholesterol esterase in a nutrient medium containing soybean meal or soybean flour, producing and accumulating cholesterol esterase and thereafter isolating said cholesterol esterase.

7. The process of claim 6, wherein said culturing is carried out at a pH of 3 to 9 and at a temperature of 20° to 40° C for 1 to 5 days.

8. The process of claim 6, wherein said nutrient medium contains additionally at least one fatty acid ester of cholesterol.

9. The process of claim 6 wherein said nutrient medium contains 0.3 to 7% by weight of soybean meal or soybean flour based on the volume of the nutrient medium.

10. The process of claim 6 wherein the nutrient medium further contains at least one member selected from fatty acids and fatty acid esters.

11. The process of claim 10 wherein the fatty acids and fatty acid esters are selected from linoleic acid, oleic acid, stearic acid, soybean oil, rice bran oil, rapeseed oil, olive oil, triolein and trilinolein.

12. The process of claim 10 wherein the nutrient medium contains 0.3 to 1.5% by weight of at least one of the fatty acids and fatty acid esters based on the volume of the nutrient medium.

13. The process of claim 1 wherein said culturing is carried out at a pH of 3 to 9 and at a temperature of 20° to 40° C for 1 to 5 days.

* * * * *